United States Patent
Yu et al.

(10) Patent No.: US 11,505,800 B2
(45) Date of Patent: Nov. 22, 2022

(54) METHOD FOR IMPROVING BIO-COUPLING EFFICIENCY BETWEEN PROTEIN AND NUCLEIC ACID BASED ON ALPHA-HELIX HANDLE

(71) Applicant: Nankai University, Tianjin (CN)

(72) Inventors: Zhongbo Yu, Tianjin (CN); Xu Li, Tianjin (CN); Xiaofeng Ma, Tianjin (CN); Lihua Qu, Tianjin (CN); Wei Huang, Tianjin (CN)

(73) Assignee: Nankai University, Tianjin (CN)

( * ) Notice: Subject to any disclaimer, the term of this patent is extended or adjusted under 35 U.S.C. 154(b) by 230 days.

(21) Appl. No.: 16/618,265

(22) PCT Filed: Sep. 23, 2019

(86) PCT No.: PCT/CN2019/107289
§ 371 (c)(1),
(2) Date: Nov. 29, 2019

(87) PCT Pub. No.: WO2020/181756
PCT Pub. Date: Sep. 17, 2020

(65) Prior Publication Data
US 2021/0332372 A1    Oct. 28, 2021

(30) Foreign Application Priority Data
Mar. 13, 2019   (CN) .......................... 201910188876.6

(51) Int. Cl.
*C12N 15/70* (2006.01)
*C07K 19/00* (2006.01)
*C12N 15/62* (2006.01)

(52) U.S. Cl.
CPC .............. *C12N 15/70* (2013.01); *C07K 19/00* (2013.01); *C12N 15/62* (2013.01)

(58) Field of Classification Search
CPC ......... C12N 15/70; C12N 15/62; C07K 19/00
See application file for complete search history.

(56) References Cited

U.S. PATENT DOCUMENTS

2018/0333484 A1   11/2018   Fairman et al.

FOREIGN PATENT DOCUMENTS

| CN | 103764665 A | 4/2014 |
| CN | 109750055 A | 5/2019 |
| WO | WO-2013-003555 A1 * | 1/2013 |

OTHER PUBLICATIONS

Marth et al. Precision Templated Bottom-Up Multiprotein Nanoassembly through Defined Click Chemistry Linkage to DNA. ACS Nano 2017, 11: 5003-5010.*
Whisstock et al. Quaterly Reviews of Biophysics, 2003, "Prediction of protein function from protein sequence and structure", 36(3):307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10: 8-9.*
Kirshenbaum et al. Biosynthesis of proteins incorporating a versatile set of phenylalanine analogs. ChemBioChem, 2002, 3(2-3): p. 235-237.*
Morten, M. et al. "Recent Advances in Covalent, Site-Specific Protein Immobilization" F1000Research, vol. 5, Sep. 12, 2016 (Sep. 12, 2016), ISSN: 2046-1402.
Kim, C.H. et al. "Protein Conjugation with Genetically Encoded Unnatural Amino Acids" Current Opinion in Chemical Biology, vol. 17, No. 3, May 9, 2013 (May 9, 2013).
Addy, P.S. et al."A Chemoselective Rapid Azo-Coupling Reaction (CRACR) for Unclickable Bioconjugation", J.Am. Chem. Soc., vol. 139, No. 34, Aug. 30, 2017 (Aug. 30, 2017), ISSN:1520-5126.

* cited by examiner

*Primary Examiner* — Iqbal H Chowdhury
(74) *Attorney, Agent, or Firm* — Bayramoglu Law Offices LLC (57) ABSTRACT

A method for improving a bio-coupling efficiency between a protein and a nucleic acid based on an α-helix handle includes the following steps. First, the handle carrying the non-natural amino acid (H-tag) is designed. Then, a recombinant expression plasmid encoding a fusion protein containing the H-tag and the protein to be tested is constructed. Subsequently, the fusion recombinant protein containing the non-natural amino acid in the H-tag is expressed and purified. Finally, the non-natural amino acid in the H-tag-fused protein and the coupling group on the nucleic acid substrate are efficiently connected by click chemistry. The α-helix handle is used to provide a controllable reaction condition on the protein surface for the non-natural amino acid, avoiding the complex structure, charge and polar nanoenvironment around the surface of the protein to be tested.

6 Claims, 3 Drawing Sheets

Specification includes a Sequence Listing.

SEQUENCE LISTING

<160> NUMBER OF SEQ ID NOS: 8

<210> SEQ ID NO 1
<211> LENGTH: 10
<212> TYPE: PRT
<213> ORGANISM: Artificial Sequence
<220> FEATURE:
<223> OTHER INFORMATION: This sequence is synthesized.

<400> SEQUENCE: 1

Asp Ile Thr Gln Gln Ala Lys Asp Ile Gly
1               5                   10

<210> SEQ ID NO 2
<211> LENGTH: 8
<212> TYPE: PRT
<213> ORGANISM: Artificial Sequence
<220> FEATURE:
<223> OTHER INFORMATION: This sequence is synthesized.

<400> SEQUENCE: 2

Gly Ser Gly Gly Gly Ser Gly Gly
1               5

<210> SEQ ID NO 3
<211> LENGTH: 30
<212> TYPE: DNA
<213> ORGANISM: Artificial Sequence
<220> FEATURE:
<223> OTHER INFORMATION: This sequence is synthesized.

<400> SEQUENCE: 3
gatataacac aacaagctaa agatataggc                                     30

<210> SEQ ID NO 4
<211> LENGTH: 24
<212> TYPE: DNA
<213> ORGANISM: Artificial Sequence
<220> FEATURE:
<223> OTHER INFORMATION: This sequence is synthesized.

<400> SEQUENCE: 4
ggtagcggtg gcggaagcgg cggt                                           24

<210> SEQ ID NO 5
<211> LENGTH: 1089
<212> TYPE: DNA
<213> ORGANISM: Artificial Sequence
<220> FEATURE:
<223> OTHER INFORMATION: This sequence is synthesized.

<400> SEQUENCE: 5
atggctgata taacacaata ggctaaagat ataggcggta gcggtggcgg aagcggcggt    60
aattatatgg gtaatccttg gacggaatat atggcaaaat atgatattga agaagttcat   120
ggttcaggta taagagtaga tttaggagaa gatgctgaag tagctggaac tcaatataga   180
cttccatcag ggaaatgtcc agtatttggt aaaggtataa ttattgagaa ttcaaatact   240
acttttttaa caccggtagc tacgggaaat caatatttaa agatggaggt tttgcttttt   300
cctccaacag aacctcttat gtcaccaatg acattagatg aaatgagaca tttttataaa   360
gataataaat gtgtaaaaaa tttagatgaa ttgactttat gttcaagaca tgcaggaaat   420
atgattccag ataatgataa aaattcaaat tataaatatc cagctgttta tgatgacaaa   480
gataaaaagt gtcatatatt atatattgca gctcaagaaa ataatggtcc tagatattgt   540

```
aataaagacg aaagtaaaag aaacagcatg ttttgtttta gaccagcaaa agatatatca    600
tttcaaaact atacatattt aagtaagaat gtagttgata actgggaaaa agtttgccct    660
agaaagaatt tacagaatgc aaaattcgga ttatgggtcg atggaaattg tgaagatata    720
ccacatgtaa atgaatttcc agcaattgat cttttgaat gtaataaatt agttttgaa      780 ttgagtgctt cggatcaacc taaacaatat gaacaacatt taacagatta tgaaaaaatt    840
aaagaaggtt tcaaaaataa gaacgctagt atgatcaaaa gtgcttttct tcccactggt    900
gcttttaaag cagatagata taaaagtcat ggtaagggtt ataattgggg aaattatacc    960
acagaaacac aaaaatgtga aatttttaat gtcaaaccaa catgtttaat taacaattca   1020
tcatacattg ctactactgc tttgtcccat cccatcgaag ttgaactcga gcaccaccac   1080
caccaccac                                                           1089

<210> SEQ ID NO 6
<211> LENGTH: 56
<212> TYPE: DNA
<213> ORGANISM: Artificial Sequence
<220> FEATURE:
<223> OTHER INFORMATION: This sequence is synthesized.

<400> SEQUENCE: 6
catgccatgg ctgatataac acaataggct aaagatatag gcggtagcgg tggcgg         56

<210> SEQ ID NO 7
<211> LENGTH: 31
<212> TYPE: DNA
<213> ORGANISM: Artificial Sequence
<220> FEATURE:
<223> OTHER INFORMATION: This sequence is synthesized.

<400> SEQUENCE: 7
ccgctcgagt tcaacttcga tgggatggga c                                    31

<210> SEQ ID NO 8
<211> LENGTH: 14
<212> TYPE: DNA
<213> ORGANISM: Artificial Sequence
<220> FEATURE:
<223> OTHER INFORMATION: This sequence is synthesized.

<400> SEQUENCE: 8
cgtctgaccg taac                                                       14
```

METHOD FOR IMPROVING BIO-COUPLING EFFICIENCY BETWEEN PROTEIN AND NUCLEIC ACID BASED ON ALPHA-HELIX HANDLE

CROSS REFERENCE TO THE RELATED APPLICATIONS

This application is the national phase entry of International Application No. PCT/CN2019/107289, filed on Sep. 23, 2019, which is based upon and claims priority to Chinese Patent Application No. 201910188876.6, filed on Mar. 13, 2019, the entire contents of which are incorporated herein by reference.

TECHNICAL FIELD

The present disclosure belongs to the field of medicinal chemistry and chemical biology, and more specifically relates to a method for improving a bio-coupling efficiency between a protein and a nucleic acid based on an alpha-helix (α-helix) handle.

BACKGROUND

Bio-coupling is an important tool for studying the interaction of biological macromolecules. Bio-coupling is particularly significant for understanding the function of the macromolecules in cell life activities and the dynamic mechanism of drugs in regulating the biological activity of the macromolecules, and has become a frontier in the crossing of the fields of medicine, chemistry and biology. Bio-coupling can occur between proteins, between protein and nucleic acid, between nucleic acids, between drug and protein, and between drug and nucleic acid. Common bio-coupling reactions include click chemistry, which can be a disulfide bond forming reaction, a maleimide reaction, and others. The groups of natural amino acids involved in protein-protein coupling include amino groups, carboxyl groups, mercapto groups and others. The natural amino acid is easy to achieve bio-coupling due to a multitude of modified group sites and a high overall reactivity of a natural amino acid. The disadvantage of the natural amino acid on the other hand, is that it has a low specificity in site selection, and the site-directed modification is almost impossible. Bioorthogonal techniques allow a cell to introduce non-natural amino acids into a protein in targeted sites by a translation means, which breaks through the limit of group selection for natural amino acids participating in the bio-coupling and greatly enriches the modified group library. Although any position of the protein can be introduced with non-natural amino acids through site-directed genetic mutations, the nanoenvironment around the surface of the protein is complex, making it difficult to predict the reactivity of the non-natural amino acids as coupling groups. The main factors affecting the reactivity of the non-natural amino acids as coupling groups include: a solvent-exposed degree at an introducing site, charge levels of the amino acid itself and the surroundings, polarity characteristics of groups adjacent to the amino acids, and others. The protein-protein coupling through the non-natural amino acids requires a complex optimization and selection process of mutation sites and has a low coupling efficiency. The bio-coupling between proteins and nucleic acids is critical for studying the interaction of the proteins with the nucleic acids. Therefore, it is necessary to develop a universal handle carrying a non-natural amino acid introduction site for an efficient bio-coupling between a protein and a nucleic acid.

SUMMARY

In order to solve the above technical problems, the present invention provides a method for improving the bio-coupling efficiency between a protein and a nucleic acid based on an α-helix handle, which is configured for an optimized design of a position of a protein coupling group, and more specifically for detection of an interaction of biological macromolecules based on a coupling reaction.

The technical solution of the present invention is as follows: a method for improving a bio-coupling efficiency between a protein and a nucleic acid based on an α-helix handle includes connecting the α-helix handle to a tail end of the protein by a connecting polypeptide, inserting a non-natural amino acid into a specific site of the α-helix handle by expanding a genetic code, and realizing an efficient bio-coupling between the protein and the nucleic acid by click chemistry.

The specific steps are as follows:

Step 1. Designing a handle carrying the non-natural amino acid (H-tag) according to an α-helix of a protein secondary structure and connecting to one tail end of the protein to be tested by a polypeptide.

Step 2. Mutating one codon of the H-tag to a non-natural amino acid codon by a site-directed mutagenesis, constructing a recombinant expression plasmid encoding a fusion protein containing the H-tag and the protein to be tested by a prokaryotic expression vector, transferring into competent cells, and then screening to obtain a cloned strain with a stable heritability.

Step 3. Co-transforming the recombinant expression plasmid encoding the fusion protein containing the H-tag and the protein to be tested with a plasmid capable of expressing a tRNA/aminoacyl tRNA synthetase to obtain a prokaryotic expression strain, adding the non-natural amino acid to a medium, and using an inducer to induce an expression of an H-tag-fused protein to be tested.

Step 4. Lysing cells of the prokaryotic expression strain after being induced for the expression, and purifying to obtain a soluble H-tag-protein to be tested by an affinity tag of the recombinant protein.

Step 5. Performing an efficient connection between the H-tag-fused protein to be tested and a coupling group of a nucleic acid substrate by click chemistry, and detecting a reaction efficiency by a gel electrophoresis.

Preferably, the non-natural amino acid is a non-natural amino acid-coupled azide group, specifically azidophenyl-alanine.

Preferably, the click chemistry is a strain-promoted alkyne-azide cycloaddition reaction.

Preferably, in step 1, the H-tag includes more than 5 amino acids in length, and is designed at an amino terminus or a carboxy terminus of the protein to be tested.

Preferably, the connecting polypeptide includes more than 8 amino acids in length;

Preferably, a preferred position of the non-natural amino acid in a sequence of the H-tag satisfies the condition of being electrically neutral, a polar amino acid environment and an amino acid value relative to a solvent accessibility being 2-3.

Preferably, in the step 2, the prokaryotic expression vector is a pET-series vector.

Preferably, the non-natural amino acid codon is an amber codon.

Preferably, the recombinant expression plasmid encoding the fusion protein containing the H-tag and the protein to be tested can be constructed by a ligation-dependent cloning method or a seamless cloning method.

Preferably, in the step 3, the medium contains 5% of glycerol by volume and 1 mM of the non-natural amino acid.

Preferably, the inducer is 1 mM of isopropyl-β-D-thiogalactopyranoside (IPTG).

Preferably, an induction expression time is preferably 12-20 h, more preferably 16 h.

Preferably, a gene encoding an orthogonal pair in the plasmid capable of expressing the tRNA/aminoacyl tRNA synthetase may be single copy or multiple copies.

Preferably, in the step 4, the cells are lysed by a protease inhibitor, and the protease inhibitor is preferably phenylmethylsulfonyl fluoride at a concentration of 0.1-1 mM;

Preferably, the affinity tag is hexahistidine or glutathione thioltransferase; Preferably, the cells are lysed by an ultrasonic cell disruptor at a power of 200 W with a cycle of 4 seconds on and 6 seconds off for a total time of 25-40 min.

Preferably, the protein is purified by a chromatographic technique, preferably an affinity chromatography, specifically a metal chelate affinity chromatography, or a complex ion exchange chromatography.

Preferably, the coupling group on the nucleic acid substrate in the step 5 is a polyethylene glycol dibenzocyclooctyne group.

Preferably, a molar ratio of the fusion protein to the nucleic acid substrate is 1:(2.5-5), preferably 1:5.

Preferably, a reaction temperature is 12° C., and a reaction time is 24 h.

Preferably, the gel electrophoresis is sodium dodecyl sulfate-polyacrylamide gel electrophoresis (SDS-PAGE), a concentration of polyacrylamide is 12% (v/v), a gel thickness is 0.75 mm, a voltage is 200 V, and an electrophoresis time is 45 min.

An α-helix handle for connecting a protein and a nucleic acid is provided, where a specific site of the α-helix handle contains a non-natural amino acid.

Preferably, the non-natural amino acid is azidophenylalanine;

Preferably, the nucleic acid is connected to a coupling group, and the coupling group is preferably a polyethylene glycol dibenzocyclooctyne group;

Preferably, the α-helix handle is connected to the protein to be tested by a connecting polypeptide.

The present invention has the following advantages and positive effects: the method uses the α-helix handle to provide a controllable reaction condition on the protein surface for the non-natural amino acid, avoiding the complex structure, charge and polar nanoenvironment around the surface of the protein to be tested, thereby achieving the objectives such as an efficient connection between the protein and the nucleic acid by click chemistry.

DETAILED DESCRIPTION OF THE EMBODIMENTS

One embodiment of the present invention is described with reference to the accompanying drawings. The experimental schemes which are not provided with specific conditions in the embodiment are performed in accordance with the reaction conditions suggested in conventional schemes or product specifications. General devices, materials, reagents, and the like in the embodiment are commercially available unless otherwise specified.

The principle of designing a handle for being coupled with protein by click chemistry is to provide the most reactive anchor for a non-natural amino acid. The secondary structure is the first element in the handle design to be coupled with protein. An α-helix provides a stable coupling reaction anchor, which is the preferred handle structure, and is denoted as H-tag. The amino acid sequence of the α-helix determines a local environment of the anchor in the protein coupling reaction.

Figure 1:
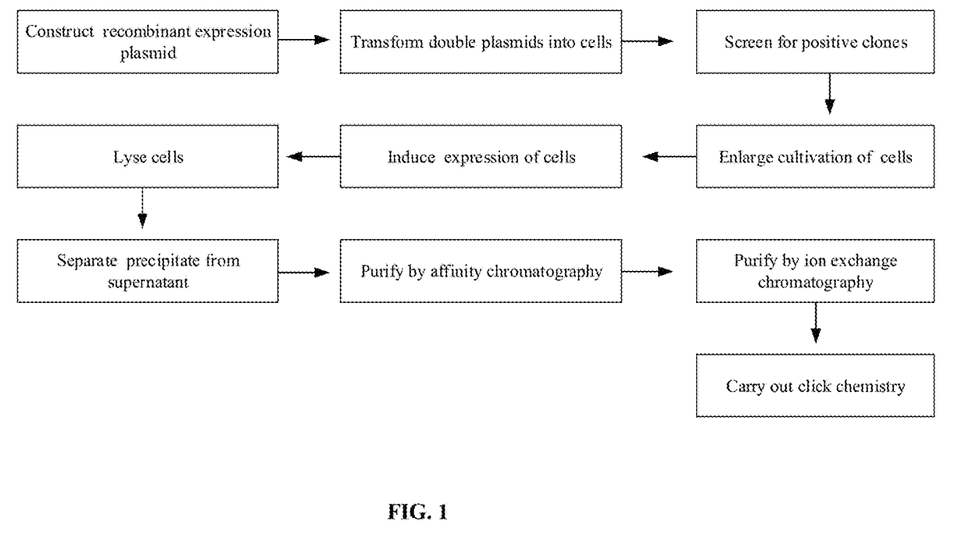
FIG. 1 shows a flow chart of a method for improving a bio-coupling efficiency between a protein and a nucleic acid based on an α-helix handle.

A method for improving a bio-coupling efficiency between a protein and a nucleic acid based on an α-helix handle includes connecting the α-helix handle with a tail end of the protein by a connecting polypeptide, inserting a non-natural amino acid into a specific site of the α-helix handle by expanding a genetic code, and realizing efficient bio-coupling of the protein with the nucleic acid by click chemistry. First, the handle H-tag carrying the non-natural amino acid codon is designed. Then, a recombinant expression plasmid encoding a fusion protein containing the H-tag and the protein to be tested is constructed. Subsequently, the fusion recombinant protein containing the non-natural amino acid in the H-tag is expressed and purified. Finally, the non-natural amino acid in the fusion protein H-tag and the coupling groups on the nucleic acid substrate are efficiently connected by click chemistry, and the flow is shown in FIG. 1.

The specific steps are as follows:

Step 1. A handle carrying the non-natural amino acid (H-tag) is designed according to an α-helix of a protein secondary structure and is connected to one tail end of the protein to be tested by a polypeptide.

Step 2. One codon of the H-tag is mutated to a non-natural amino acid codon by a site-directed mutagenesis, a recombinant expression plasmid encoding a fusion protein containing the H-tag and the protein to be tested is constructed by a prokaryotic expression vector, transferred into competent cells, and is then screened to obtain a cloned strain with a stable heritability.

Step 3. The recombinant expression plasmid encoding the fusion protein containing the H-tag and the protein is co-transformed with a plasmid capable of expressing a tRNA/aminoacyl tRNA synthetase to obtain a prokaryotic expression strain. The non-natural amino acid is added to a medium, and an inducer is used to induce an expression of an H-tag-fused protein to be tested.

Step 4. Cells of the prokaryotic expression strain after being induced for the expression are lysed, and purified to obtain a soluble H-tag-fused protein to be tested by an affinity tag of the recombinant protein.

Step 5. An efficient connection between the H-tag-fused protein to be tested and the coupling groups on a nucleic acid substrate is performed by the click chemistry, and the reaction efficiency is detected by gel electrophoresis.

Further, the non-natural amino acid is a non-natural amino acid-coupled azide group, specifically azidophenylalanine. Correspondingly, the click chemistry is a strain-promoted alkyne-azide cycloaddition reaction, and the H-tag-fused protein to be tested is rapidly connected to the nucleic acid substrate by the azide group and a dibenzocyclooctyne group. The H-tag includes more than 5 amino acids and less than 30 amino acids in length and is connected to an amino terminus or a carboxy terminus of the protein to be tested. If the H-tag includes less than 5 amino acids, it may disrupt the α-helix secondary structure when mutations are performed on the α-helix. If the H-tag includes more than 30 amino acids in length, the connection effect will decrease. The connecting polypeptide includes more than 8 amino acids and less than 20 amino acids in length. If the connecting polypeptide includes less than 8 amino acids, it is unable to act as an isolation from the amino acid environment on the protein surface. Moreover, a preferred position of the non-natural amino acid in a sequence of the H-tag satisfies the condition of being electrically neutral, a polar amino acid environment and a moderate surface-exposed degree, where the surface-exposed degree can be achieved through the online software SABLE, and the value of relative solvent accessibility of the amino acids is predicted within a total range of 0-5. In the present solution, the amino acid residue with a value of 2 or 3 is selected as a candidate mutation site. One codon of the H-tag is mutated to a non-natural amino acid codon by site-directed mutagenesis. The codon of the non-natural amino acid may be an amber codon or other codon capable of inserting the non-natural amino acid.

The principle of designing a handle for being coupled with protein by click chemistry is to provide the most reactive anchor for a non-natural amino acid. The secondary structure is the first element in the design of the handle for being coupled with protein. The α-helix provides a stable coupling reaction anchor, which is the preferred handle structure, and is denoted as H-tag. The amino acid sequence of the α-helix determines a local environment of the anchor in the protein coupling reaction.

The specific steps are as follows:

Step 1. A handle carrying the azidophenylalanine (H-tag) is designed according to an α-helix of a protein secondary structure and is connected to one tail end of the protein to be tested by a polypeptide. The H-tag is designed as shown in SEQ ID NO: 1, and the connecting peptide is designed as shown in SEQ ID NO: 2.

```
                                      SEQ ID NO: 1
      DITQQAKDIG

SEQ ID NO: 2
      GSGGGSGG
```

The nucleic acid sequence of the H-tag, as shown in SEQ ID NO: 3, is placed at the 5' end of the nucleic acid sequence of the protein to be tested for connection with a nucleic acid sequence encoding a connecting peptide, as shown in SEQ ID NO: 4, between the H-tag and the protein to be tested to form a complete fusion protein.

```
                                      SEQ ID NO: 3
      GATATAACACAACAAGCTAAAGATATAGGC

SEQ ID NO: 4
      GGTAGCGGTGGCGGAAGCGGCGGT
```

Figure 4:
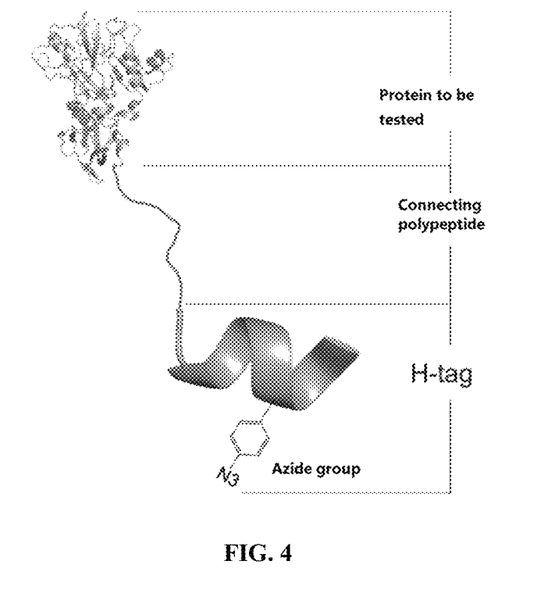
FIG. 4 is a structural schematic diagram of an H-tag-fused protein in embodiment 1.

Step 2. One codon of the H-tag is mutated to the amber codon or other codon capable of inserting the non-natural amino acid by site-directed mutagenesis, the structure thereof is shown in FIG. 4. For example, the 5th Gln codon in the nucleotide sequence encoding the H-tag amino acid sequence is genetically mutated to TAG for introducing azidophenylalanine. Then, a recombinant expression plasmid encoding a fusion protein containing the H-tag and the protein to be tested is constructed by the nucleotide sequence and a prokaryotic expression vector, and is transferred into competent cells and then screened to obtain a cloned strain with a stable heritability.

Specifically, the prokaryotic expression vector may be a pET-series prokaryotic expression vector. The competent cells for screening the cloned strain may be *Escherichia coli* (*E. coli*) DH5a cells or other *E. coli* strains performing the same function. The recombinant expression plasmid may be constructed by a T4 ligase ligation after a restriction endonuclease digestion, or a ligation-independent cloning such as seamless cloning.

Step 3. The recombinant expression plasmid encoding the fusion protein containing the H-tag and the protein is extracted from the cloned strain, and is co-transformed with a plasmid capable of expressing a tRNA/aminoacyl tRNA synthetase to obtain a prokaryotic expression strain. The non-natural amino acid and 4-azido-L-phenylalanine are added to a medium containing the prokaryotic expression strain, and an inducer is used to induce an expression of the H-tag-fused protein to be tested.

Figure 3:
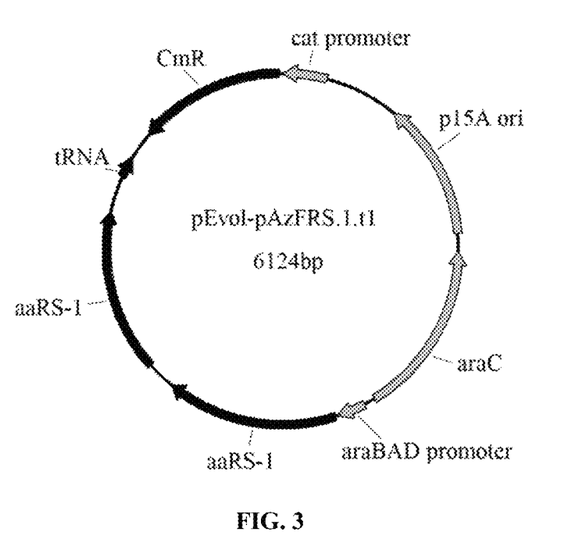
FIG. 3 is a diagram of a pEvol-pAzFRS.1.t1 plasmid encoding tRNA/aminoacyl tRNA synthetase.

Specifically, the medium contains 5% glycerol by volume and 1 mM of 4-azido-L-phenylalanine. The inducer is 1 mM of IPTG. The induction expression time is preferably 12-20 h. The gene encoding an orthogonal pair in the plasmid capable of expressing the tRNA/aminoacyl tRNA synthetase may be single copy or multiple copies for introducing the non-natural amino acid. The plasmid used in the present solution is the plasmid pEvol-pAzFRS.1.t1 encoding the tRNA/aminoacyl tRNA synthetase, purchased from "National Collection of Type Cultures (NCTC), Item No.: Plasmid 73547", and the structure is shown in FIG. 3.

Step 4. Cells of the prokaryotic expression strain after being induced for the expression are lysed, and purified to obtain a soluble H-tag-fused protein to be tested by an affinity tag of the recombinant protein.

The cells are lysed under an action of a protease inhibitor, and the protease inhibitor is preferably phenylmethylsulfonyl fluoride (PMSF) at a concentration of 0.1-1 mM, or may be other protease inhibitors. The cells are lysed by an ultrasonic cell disruptor at a power of 200 W with a cycle of 4 seconds on and 6 seconds off for a total time of 25-40 min. The affinity tag is hexahistidine or glutathione thioltransferase (GST), or other tags with the similar function. The protein is purified by a chromatographic technique, and the chromatographic technique may be an affinity chromatography such as a metal chelate affinity chromatography, or a complex ion exchange chromatography.

Figure 6:
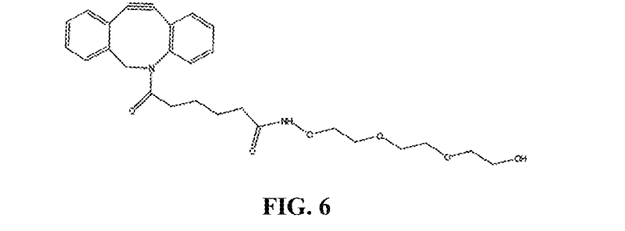
FIG. 6 shows a structure of a single stranded nucleic acid modified with dibenzocyclooctyne (DBCO) in embodiment 1.
Figure 7:
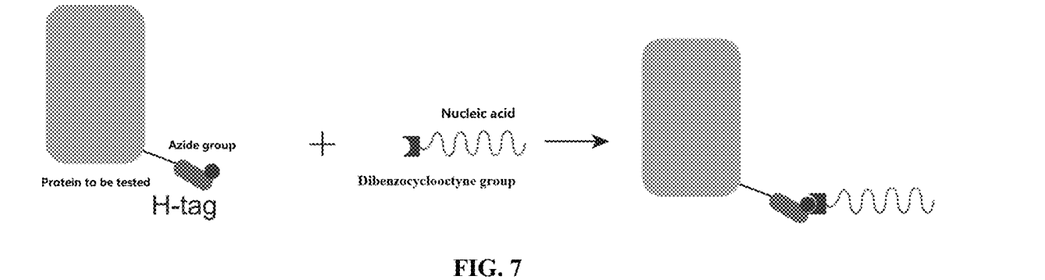
FIG. 7 is a schematic diagram of a strain-promoted alkyne-azide cycloaddition reaction in embodiment 1.

Step 5. An efficient connection between the H-tag-fused protein to be tested and coupling group on the nucleic acid substrate is performed by a strain-promoted alkyne-azide cycloaddition reaction, and the reaction schematic diagram is shown in FIG. 7. The coupling group on the nucleic acid substrate is a polyethylene glycol dibenzocyclooctyne group, as shown in FIG. 6. A molar ratio of the fusion protein to the nucleic acid substrate is 1:(2.5-5), preferably 1:5. The reaction temperature is 12° C., and the reaction time is 24 h. The reaction efficiency is detected by gel electrophoresis. The gel electrophoresis is sodium dodecyl sulfate-polyacrylamide gel electrophoresis, the concentration of polyacrylamide is 12% (v/v), the gel thickness is 0.75 mm, the voltage is 200 V, and the electrophoresis time is 45 min.

The present invention has certain universality, and is particularly suitable for soluble proteins and inclusion body proteins. The PfAMA1 protein is taken as an example to describe the solution of the present invention in detail. The experimental schemes which are not provided with specific conditions in the embodiment are performed in accordance with the reaction conditions suggested in conventional schemes or product specifications. General devices, materials, reagents, and the like in the embodiment are commercially available unless otherwise specified.

Embodiment: Application of H-Tag in Efficient Bio-Coupling Between PfAMA1 Protein and Single-Stranded Nucleic Acid 1. H-Tag Design The sequence of the H-tag is designed as SEQ ID NO: 1 to provide moderate surface-exposed degree, electrical neutrality and polar amino acid environment for the non-natural amino acid azidophenylalanine in a coupling reaction with protein. The connecting peptide is designed to have a sequence as shown in SEQ ID NO: 2 as a linker or bridge to connect the protein to the H-tag (helical tag), allowing to isolate the target protein to be tested from the handle for coupling by click chemistry, thereby reducing the influence of the complex environment around the protein surface on the connection efficiency.

```
                                            SEQ ID NO: 1
DITQQAKDIG

SEQ ID NO: 2
GSGGGSGG
```

Figure 5:
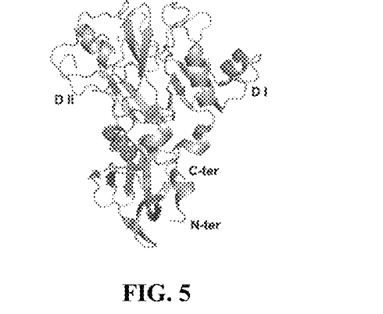
FIG. 5 is a diagram showing a three-dimensional structure of a protein PfAMA1 to be tested in embodiment 1.

The nucleic acid sequence of the H-tag, as shown in SEQ ID NO: 3, is placed at the 5' end of the nucleic acid sequence of the protein to be tested PfAMA1 (the structure is shown in FIG. 5) for connection with a nucleic acid sequence encoding a connecting peptide having a sequence as shown in SEQ ID NO: 4 between the H-tag and PfAMA1 to form a sequence encoding the complete fusion protein, and the sequence of the fusion protein is shown in SEQ ID NO: 5. Among them, the $5^{th}$ Gln codon in the nucleotide sequence encoding the H-tag amino acid sequence is genetically mutated to TAG (amber codon) for introducing azidophenylalanine.

```
                                            SEQ ID NO: 3
GATATAACACAACAAGCTAAAGATATAGGC

SEQ ID NO: 4
GGTAGCGGTGGCGGAAGCGGCGGT

SEQ ID NO: 5
atggctgatataacacaataggctaaagatataggcggtagcggtggcg gaagcggcggtaattatatgggtaatccttggacggaatatatggcaaa atatgatattgaagaagttcatggttcaggtataagagtagatttagga gaagatgctgaagtagctggaactcaatatagacttccatcagggaaat gtccagtatttggtaaaggtataattattgagaattcaaatactactttt tttaacaccggtagctacgggaaatcaatatttaaaagatggaggttt gcttttcctccaacagaacctcttatgtcaccaatgacattagatgaaa tgagacatttttataaagataataaatgtgtaaaaaatttagatgaatt gactttatgttcaagacatgcaggaaatatgattccagataatgataaa aattcaaattataaatatccagctgtttatgatgacaaagataaaaagt gtcatatattatatattgcagctcaagaaaataatggtcctagatattg taataaagacgaaagtaaaagaaacagcatgttttgttttagaccagca aaagatatatcatttcaaaactatacatatttaagtaagaatgtagttg ataactgggaaaaagtttgccctagaaagaatttacagaatgcaaaatt cggattatgggtcgatggaaattgtgaagatataccacatgtaaatgaa tttccagcaattgatattttgaatgtaataaaattagttttttgaattgag tgatcggatcaacctaaacaatatgaacaacatttaacagattatgaaa aaattaaagaaggtttcaaaaataagaacgctagtatgatcaaagtgc ttttcttcccactggtgcttttaaagcagatagatataaagtcatggt aagggtataattgggaaattataccacagaaacaaaaatgtgaaa tttttaatgtcaaaccaacatgtttaattaacaattcatcatacattgc tactactgctttgtcccatcccatcgaagttgaactcgagcaccaccac caccaccac
```

2. Construction of Expression Vector of Fusion Recombinant Protein PfAMA1 with H-Tag Sequence at the Amino Terminus The desired sequence is obtained by polymerase chain reaction (PCR) with the sequence encoding fusion protein as a template, an upstream primer (such as SEQ ID NO: 6) and a downstream primer (such as SEQ ID NO: 7). The upstream primer includes a restriction endonuclease NcoI site and the downstream primer includes a restriction endonuclease XhoI site. The desired sequence (5 μg) and *E. coli* prokaryotic expression vector pET-21d (5 μg) are digested with a NcoI restriction endonuclease (10 U) and a XhoI restriction endonuclease (10 U) in a 50 μl solution containing buffer solution (including 10 mM Tris-HCl, (pH 8.5), 10 mM of $MgCl_2$, 100 mM of KCl, and 0.1 mg/mL of bovin serum albumin (BSA)) for 1 h at 37° C. After the separation by 1% agarose gel electrophoresis (120 V, 20 min), the gel is cut for recycle and purification is performed to obtain the desired sequence and vector containing the sticky ends. In 10 μl solution containing buffer solution (including 40 mM of Tris-HCl, 10 mM of $MgCl_2$, 10 mM of dithiothreitol (DTT), and 0.5 mM of ATP), the recombinant expression plasmid H-tag-PfAMA1-pET-21d is constructed by ligating the desired sequence (30 ng) with the vector (51 ng) by using T4 DNA ligase (1 U), and the plasmid contains an ampicillin-encoding gene used for screening positive clones.

SEQ ID NO: 6

CATGCCATGGCTGATATAACACAATAGGCTAAAGATATAGGCGGTAGCGGTGGCGG

SEQ ID NO: 7

CCGCTCGAGTTCAACTTCGATGGGATGGGAC

3. Expression of Recombinant Protein H-Tag-PfAMA1

Figure 2:
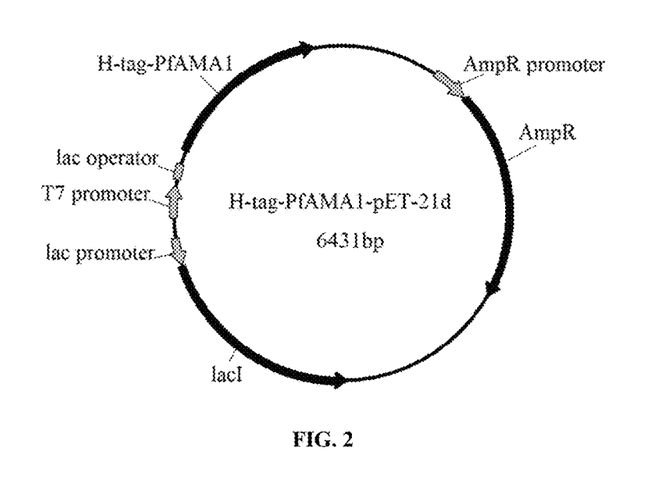
FIG. 2 is a diagram of an H-tag-PfAMA1-pET-21d recombinant expression plasmid.

The recombinant expression plasmid H-tag-PfAMA1-pET-21d (shown in FIG. 2) is co-transformed into E. coli component cells BL21 (DE3) with the plasmid pEvol-pAzFRS.1.t1 (shown in FIG. 3) encoding the tRNA/aminoacyl tRNA synthetase. The transformation method is referred to "Molecular Cloning: A Laboratory Manual (Third Edition)" (Science Press 2002, translated by HUANG Pei-tang et al). Single positive clone is elected and inoculated in 5 ml of Lysogeny broth (LB) medium containing 100 μg/ml ampicillin and 20 μg/ml chloramphenicol, followed by shaking on a constant temperature shaker (220 rpm) at 220° C. for culturing for 12 h. The bacterial liquid is transferred to 1 L of a LB medium containing $100_N$g/ml ampicillin and 20 μg/ml chloramphenicol, and is continuously cultured on the constant temperature shaker (220 rpm) at 37° C. When the optical density $OD_{600}$ of the bacterial liquid reaches 0.6-0.8, IPTG having a final concentration of 1 mM, 4-azido-L-phenoalanine having a final concentration of 1 mM and 5% glycerol are added. The expression is induced for 16 h at 37° C. on the constant temperature shaker (220 rpm). The cells are collected by centrifugation at 4000 rpm, and resuspended in a lysis buffer (including 20 mM of Tris-HCl, pH 8.0, 400 mM of NaCl, and 5% glycerol), and the cell suspension is directly used in the next purification experiment or stored at −80° C.

4. Purification of Recombinant Protein H-Tag-PfAMA1

The cell suspension in the step 3 is added with ethylenediaminetetraacetic acid (EDTA) having a final concentration of 2 mM, phenylmethylsulfonyl fluoride (PMSF) having a final concentration of 0.2 mM and 0.1% Triton X-100 to form 100 ml of mixed solution. The cells are sufficiently lysed by an ultrasonic cell disruptor (Ningbo Xinzhi Biotechnology Co., Ltd., Model NO.: SCIENTZ-IID) at a power of 200 W with a cycle of 4 seconds on and 6 seconds off for a total time of 40 min. The cell lysis solution is centrifuged at 18,000 rpm for 40 min, and the supernatant is discarded and the precipitated protein is kept. The precipitated protein is washed twice with 40 ml of washing buffer (including 20 mM of Tris-HCl, pH 8.0, 2 M of urea, and 0.5 mM of EDTA). The precipitated protein is dissolved in 50 ml of dissolving buffer (including 20 mM of Tris-HCl, pH 8.0, 6 M of guanidine hydrochloride (GdnHCl), 2 mM of 2-mercaptoethanol (2-ME) for 12 h. The solution is centrifuged at 18,000 rpm for 40 min, the dissolved protein in the supernatant is collected, and the precipitate is discarded. The protein solution is adjusted to a concentration of 20 μg/ml with a buffer solution (including 20 mM of Tris-HCl, pH 8.0, 6 M of GdnHCl) to form 50 ml of protein solution. A dialysis bag containing the protein solution is placed in 3 L of renaturing buffer (including 20 mM of Tris-HCl, pH 8.0, 0.5 mM of EDTA, 1 M of urea, 200 mM of NaCl, 2 mM of 2-ME, and 0.2 mM of cystamine-HCl), and is dialyzed under stirring at 4° C. for 12 h for renaturation. After the renaturation is completed, the protein solution is transferred to 3 L of the lysis buffer, and dialyzed under stirring for 12 h at 4° C. The protein precipitated by misfolding is removed by centrifugation at 18,000 rpm for 40 min. The supernatant is taken and passed through a 3 ml Ni affinity column, and then incubated at 4° C. for 3 h. The undesired protein is washed away with a lysis buffer containing 20 mM of imidazole. The desired protein is eluted with a lysis buffer containing 500 mM of imidazole. The eluted protein solution is dialyzed into 3 L of anion exchange chromatography binding buffer (including 20 mM of Tris-HCl, pH 8.0, and 40 mM of NaCl), and is dialyzed under stirring for 12 h at 4° C. Subsequently, the protein solution is purified by anion exchange chromatography and cation exchange chromatography to obtain the desired protein, and the desired protein is stored in a storage buffer (including 20 mM of Tris-HCl, pH 8.0, 200 mM of NaCl, and 5% glycerol) at −80° C.

5. Click Chemical Coupling of H-Tag-PfAMA1 with Single-Stranded DNA (ssDNA)

Figure 8:
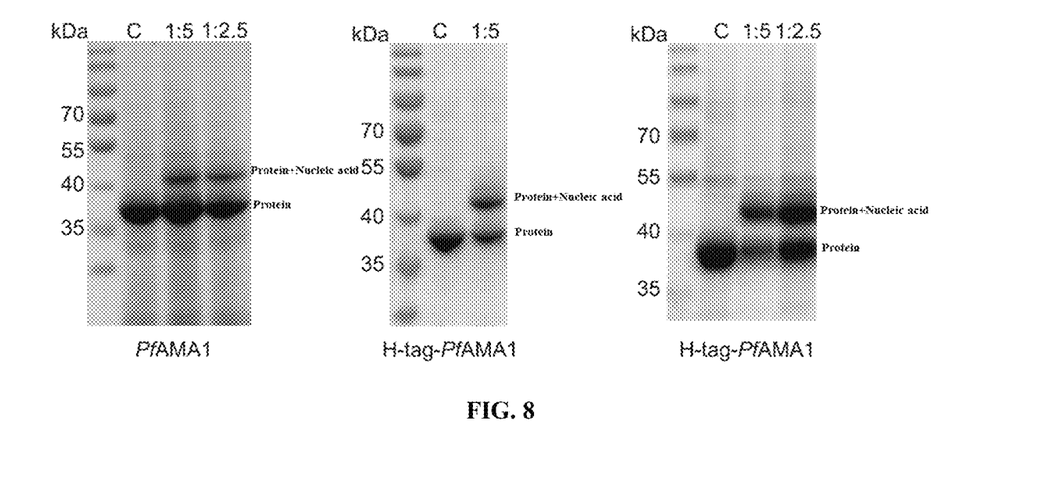
FIG. 8 is an electrophoretogram of SDS-PAGE in embodiment 1.

One of the reaction substrates of the click chemistry is ssDNA, as shown in SEQ ID NO: 8, which is synthesized by a commercial company and has a length of 14 deoxyribonucleotides where 3' end thereof is modified with a single dibenzocyclooctyne-polyethylene glycol (DBCO-PEG) (as shown in FIG. 6). The protein is taken from the −80° C. refrigerator and is thawed on ice. The protein and the ssDNA are mixed at a molar ratio of 1:5 and 1:2.5, respectively. When the molar ratio is 1:5, final concentrations of the protein and the ssDNA are 40 μM and 200 μM, respectively. When the molar ratio is 1:2.5, final concentrations of the protein and the ssDNA are 80 μM and 200 μM, respectively. The final volume of reaction solution is adjusted to 5 μl by adding a buffer solution (including 20 mM of Tris-HCl, pH 8.0, and 200 mM of NaCl), and the reaction solution is repeatedly blown 10 times by a pipette until evenly mixed, followed by reacting at 12° C. for 25 h. The reaction product by the click chemistry is identified by SDS-PAGE. The thickness of the 12% gel is 0.75 mm. The voltage is 200 volts, the current is 400 mA, and the electrophoresis time is 40 min. A staining is carried out with a Coomassie brilliant blue R-250 staining solution (including 0.1% (w/v) Coomassie brilliant blue R-250, 25% isopropanol (v/v), and 10% glacial acetic acid (v/v)) for 10 min. A decolorization is carried out in a Coomassie brilliant blue destaining solution (including 10% acetic acid (v/v), and 5% ethanol (v/v)). The decolorization is continued until a clear protein band is observed and background color is basically removed. A versatile imaging system (SYNGENE, model: PXi903030611) is used to take photos. As shown in FIG. 8, the protein substrate whose mutation site is selected to introduce azidophenylalanine inside the PfAMA1 is subjected to a click chemical reaction with the ssDNA, and the yield is 10%. The H-tag is introduced at the amino terminus of the PfAMA1, and azidophenylalanine site-directed mutagenesis is carried out on the H-tag, and the yield of the click chemical reaction with the ssDNA is 50%. In contrast, the bio-coupling efficiency of the H-tag-fused protein is improved by 40%.

SEQ ID NO: 8

CGTCTGACCGTAAC

The embodiment of the present invention is described in detail above, but the above description is only a preferred embodiment, and is not intended to limit the scope of the present invention. All changes and improvements made in accordance with the scope of the present invention should still fall within the scope of the present invention.

What is claimed is:

1. A method for improving a bio-coupling efficiency between a protein and a nucleic acid based on an α-helix handle, comprising: connecting the α-helix handle to a tail end of the protein by a connecting polypeptide, inserting a non-natural amino acid into a specific site of the α-helix handle by expanding a genetic code, and realizing a bio-coupling of the protein with the nucleic acid by click chemistry,
wherein
the α-helix handle is a helical tag (H-tag), wherein an amino acid sequence of the H-tag is set forth in SEQ ID NO: 1, and the H-tag is provided at an amino terminus or a carboxy terminus of the protein to be tested;
an amino acid sequence of the connecting polypeptide is set forth in SEQ ID NO: 2;
the non-natural amino acid is azidophenylalanine, wherein a position of the non-natural amino acid in the amino acid sequence of the H-tag satisfies conditions of being electrically neutral, a polar amino acid environment, and an amino acid value relative to a solvent accessibility being 2-3; and
the click chemistry is a strain-promoted alkyne-azide cycloaddition reaction.

2. The method according to claim 1, further comprising:
1) designing the H tag according to an α-helix of a protein secondary structure, and connecting the H-tag to the tail end of the protein to be tested by the connecting polypeptide;
2) mutating one codon of the H-tag to a non-natural amino acid codon by a site-directed mutagenesis, constructing a recombinant expression plasmid encoding a fusion protein containing the H-tag and the protein to be tested by a prokaryotic expression vector, transferring into competent cells, and then screening to obtain a cloned strain with a stable heritability;

3) co-transforming the recombinant expression plasmid encoding the fusion protein containing the H-tag and the protein to be tested with a plasmid configured for expressing tRNA and aminoacyl tRNA synthetase to obtain a prokaryotic expression strain, adding the non-natural amino acid to a medium, and using an inducer to induce an expression of an H-tag-fused protein to be tested;
4) lysing cells of the prokaryotic expression strain after being induced for the expression, and purifying to obtain a soluble H-tag-fused protein to be tested by an affinity tag of the recombinant protein; and
5) performing an efficient connection between the H-tag-fused protein to be tested and a coupling group on a nucleic acid substrate by the click chemistry, and detecting a reaction efficiency by a gel electrophoresis.

3. The method according to claim 2, wherein in the step 2,
the prokaryotic expression vector is a pET-series vector;
the non-natural amino acid codon is an amber codon; and
the recombinant expression plasmid encoding the fusion protein containing the H-tag and the protein to be tested is constructed by a ligation-dependent cloning method or a seamless cloning method.

4. The method according to claim 2, wherein in the step 3,
the medium contains 5% glycerol by volume and 1 mM of the non-natural amino acid;
the inducer is 1 mM of isopropyl-β-D-thiogalactopyranoside (IPTG);
an induction expression time is 12-20 h; and
a gene encoding an orthogonal pair in the plasmid configured for expressing the tRNA and the aminoacyl tRNA synthetase is a single copy or multiple copies.

5. The method according to claim 2, wherein in the step 4,
the cells are lysed under an action of a protease inhibitor, and the protease inhibitor is phenylmethylsulfonyl fluoride at a concentration of 0.1-1 mM;
the affinity tag is hexahistidine or glutathione thioltransferase;
the cells are lysed by an ultrasonic cell disruptor at a power of 200 W with a cycle of 4 seconds on and 6 seconds off for a total time of 25-40 min; and
the protein is purified by a metal chelate affinity chromatography, or a complex ion exchange chromatography.

6. The method according to claim 2, wherein in the step 5,
the coupling group on the nucleic acid substrate is a polyethylene glycol dibenzocyclooctyne group;
a molar ratio of the H-tag-fused protein to the nucleic acid substrate is 1:(2.5-5);
a reaction temperature is 12° C., and a reaction time is 24 h; and
the gel electrophoresis is sodium dodecyl sulfate-polyacrylamide gel electrophoresis, a concentration of polyacrylamide is 12% by volume, a gel thickness is 0.75 mm, a voltage is 200 V, and an electrophoresis time is 45 min.

* * * * *